US006654633B2

(12) United States Patent
Stengel et al.

(10) Patent No.: US 6,654,633 B2
(45) Date of Patent: Nov. 25, 2003

(54) MOBILE NEUROLOGICAL SIGNAL DATA ACQUISITION SYSTEM AND METHOD

(75) Inventors: Keith A. Stengel, Tucson, AZ (US); Steve G. E. Franks, Tucson, AZ (US)

(73) Assignee: Neuralynx, Inc., Tucson, AZ (US)

( * ) Notice: Subject to any disclaimer, the term of this patent is extended or adjusted under 35 U.S.C. 154(b) by 0 days.

(21) Appl. No.: 10/047,205

(22) Filed: Nov. 7, 2001

(65) Prior Publication Data

US 2003/0088161 A1 May 8, 2003

(51) Int. Cl.[7] .................................................. A61B 5/04
(52) U.S. Cl. ........................................ 600/544; 600/300
(58) Field of Search ................................ 600/544–545, 600/300

(56) References Cited

U.S. PATENT DOCUMENTS

| | | |
|---|---|---|
| 4,037,586 A | 7/1977 | Grichnik |
| 4,140,997 A | 2/1979 | Brady |
| 4,416,288 A | 11/1983 | Freeman |
| 4,417,591 A | 11/1983 | Culver |
| 4,421,122 A | 12/1983 | Duffy |
| 4,498,080 A | 2/1985 | Culver |
| 4,649,482 A | 3/1987 | Raviv et al. |
| 4,736,307 A | 4/1988 | Salb |
| 4,744,029 A | 5/1988 | Raviv et al. |
| 4,819,648 A * | 4/1989 | Ko ............................ 600/409 |
| 4,862,359 A | 8/1989 | Trivedi et al. |
| 5,038,782 A * | 8/1991 | Gevins et al. ............... 600/383 |
| 5,381,804 A * | 1/1995 | Shambroom ................. 600/544 |
| 5,511,553 A * | 4/1996 | Segalowitz .................. 382/156 |
| 5,755,230 A * | 5/1998 | Schmidt et al. .............. 600/544 |
| 5,871,451 A * | 2/1999 | Unger et al. ................ 600/509 |
| 6,042,548 A | 3/2000 | Guiffre |
| 6,052,619 A | 4/2000 | John |
| 6,061,593 A | 5/2000 | Fischell et al. |
| 6,171,239 B1 * | 1/2001 | Humphrey ................... 600/372 |
| 6,445,940 B1 * | 9/2002 | Gevins et al. ............... 600/382 |

* cited by examiner

Primary Examiner—Robert L. Nasser
Assistant Examiner—Patricia C. Mallari
(74) Attorney, Agent, or Firm—Birdwell, Janke & Durando, PLC

(57) ABSTRACT

A mobile neurological data acquisition system. A multiplexing circuit is utilized to combined multiple electrical-neurological signal inputs (synaptic "spikes", EEG, EKG, EMG). A programmable logic device is utilized to package the combined signal into a packet containing a header and a footer. An analog transmitter is utilized to modulate a RF signal with the packetized combined signal and broadcast it to an analog receiver, where it is demodulated. An analog-to-digital converter is used to convert the demodulated combined analog signal into a combined digital signal. A computer and software algorithms are used to demultiplex the combined digital signal into discrete digital representations of the original electrical-neurological signals. The discrete digital signals are sent to a printer or video display for human analysis or stored on digital media such as a hard disk, a floppy disk, a magnetic tape, or a CD-ROM.

13 Claims, 15 Drawing Sheets

MOBILE NEUROLOGICAL SIGNAL DATA ACQUISITION SYSTEM AND METHOD

BACKGROUND OF THE INVENTION

This invention relates to neurological signal data acquisition systems, and particularly to devices which monitor electrical-neurological information and transmit representative information to a central location for analysis.

In the study of animal behavior and stimuli response, there is a desire to monitor the electrical-neurological signals referred to as synaptic response "spikes", electroencephalographic ("EG") signals, electromyographic ("EMG") signals, or electrocardiographic ("EKG") signals of mobile animals such as rats, mice, monkeys and fish in their natural environment. There also exists a desire to study the electrical-neurological signals of mobile human test subjects, without binding them to bulky, stationary test equipment or confining them to a laboratory. There is a further desire to study the electrical-neurological signals of human patients in remote locations, such as accident sites or battle-field environments. Previous approaches have had limited range dictated by wires or short range radio transmitters. Attempts to utilize radio transmitters have involved utilizing analog sensors, A-D converters, and digital transmitters to broadcast information to a central location. However, A-D conversion prior to transmission requires complex circuitry with relatively large size, weight, and power usage.

These previous approaches are found not to be practical for studying small test animals such as rats, mice and fish. Additionally, these previous approaches are too complex and bulky to operate in a non-laboratory environment, especially if numerous signals are required. A typical electrical-neurological signal acquisition system includes a probe connected to a buffer amplifier (pre-amp). These pre-amps are connected by long wires to differential amplifiers. Output from the differential amplifiers is passed through analog filters and processed by an A-D converter. Digitized data is then sent to a computer processor where it is placed in digital storage or displayed for human analysis.

One prior patent, John U.S. Pat. No. 6,052,619, describes a portable EEG instrument for use in emergencies and brain assessments. This portable EEG instrument replaced the long wires of a typical neurological data acquisition system with a digital transmitter. A headband containing one or a few EEG electrodes is placed on the head of the patient. The electrodes are connected to pre-amplifiers which are, in turn, connected to differential amplifiers. The output from the amplifiers is processed by an A-D converter. The digital information is then transmitted using a digital transmitter. A receiver unit is monitored by a trained individual. The receiver unit has a digital radio receiver with a demodulator, an amplifier and filters to separate demodulated signals into bands. A dial on the receiver unit is used to select a signal band and output the band to a speaker. The individual monitoring the speaker is trained to interpret output from the speaker representative of the electrical-neurological signals detected by the probes of the headband. The A-D converter and digital transmitter and receiver eliminate the need for wires to connect the detection equipment (probes, amplifiers) to the central analyzer (filter, dial, speaker). Information of interest is converted from A-D form prior to digital transmission at the location of the patient. This requires complex circuitry with associated size, weight and power requirements at the site of the patient. It would be desirable to move A-D conversion to the site of the central analyzer where size, weight, and power resources are not as constrained as at the remote patient location.

Accordingly, there is a need for a mobile electrical-neurological data acquisition system that is small and light enough to be worn by small test animals such as rats, mice, monkeys, and various fish in their natural environments and by human test subjects and patients away from a laboratory or hospital. There is also a need for a mobile electrical-neurological data acquisition system with a significant range (600–1000 feet) to monitor animals in their natural environment, monitor mobile human test subjects, and monitor patients in remote locations. An additional need exists for a mobile electrical-neurological data acquisition system that accepts numerous electrical-neurological signals from probes, amplifies the representative analog data signals, modulates a carrier wave with the analog data signals, and broadcasts the resulting modulated signal to a processing station. Yet another need exits for a processing station to receive a broadcast modulated signal, demodulate the analog data signals and convert the analog data signals to digital signals prior to digital storage or display for human analysis.

SUMMARY OF THE INVENTION

The present invention meets the aforementioned needs by connecting numerous electrical-neurological probes to amplifiers to produce amplified analog signal representations. The amplified signals are processed by a multiplexor to produce a combined analog signal that is modulated and broadcast using an analog transmitter. The modulating signal is encoded and applied to the transmitter so as to ensure that amplitude levels can be determined properly at the receiver. After reception and demodulation by an analog receiver, the combined analog signal is converted to a combined digital signal using an A-D converter ("ADC"). To obtain the original electrical-neurological signal representations, a computer processor applies software algorithms to de-multiplex the combined digital signal. The result is a separate digital signal representation for each of the electrical-neurological signals monitored by the probes. The separate digital signals are available for human analysis or can be stored on a digital device such as a hard drive for later analysis.

Should the number of electrical-neurological signals be too numerous to combine using a single multiplexor, the signals can be processed in hierarchical stages. The amplified electrical-neurological signals are grouped into subsets, each subset being processed by a first level multiplexor to produce a first level combined signal. The first level combined signals are processed by a second level multiplexor to produce a second level combined signal, encompassing all electrical-neurological signals. The second level combined signal is modulated and broadcast using an analog transmitter. Likewise, additional levels can be added to accommodate even more electrical-neurological signals.

Accordingly, it is a principle object of the present invention to provide a novel and improved neurological signal data acquisition system and method.

It is another object of the present invention to provide a system and method for combined multiplexed analog representation of numerous electrical-neurological signals suitable for modulation and transmission by a single channel radio frequency analog transmitter.

It is a further object of the present invention to provide a system and method that receives the combined signal and produces therefrom a separate digital representation for each electrical-neurological signal monitored by the probes.

It is yet a further object of the present invention to provide a novel physical package for mounting a portion of a neurological signal data acquisition system on an animal or patient.

The foregoing and other objects features, and advantages of the invention will be more readily understood upon consideration of the following detailed description of the invention, taken in conjunction with the accompanying drawings.

DETAILED DESCRIPTION OF THE INVENTION

Figure 1:
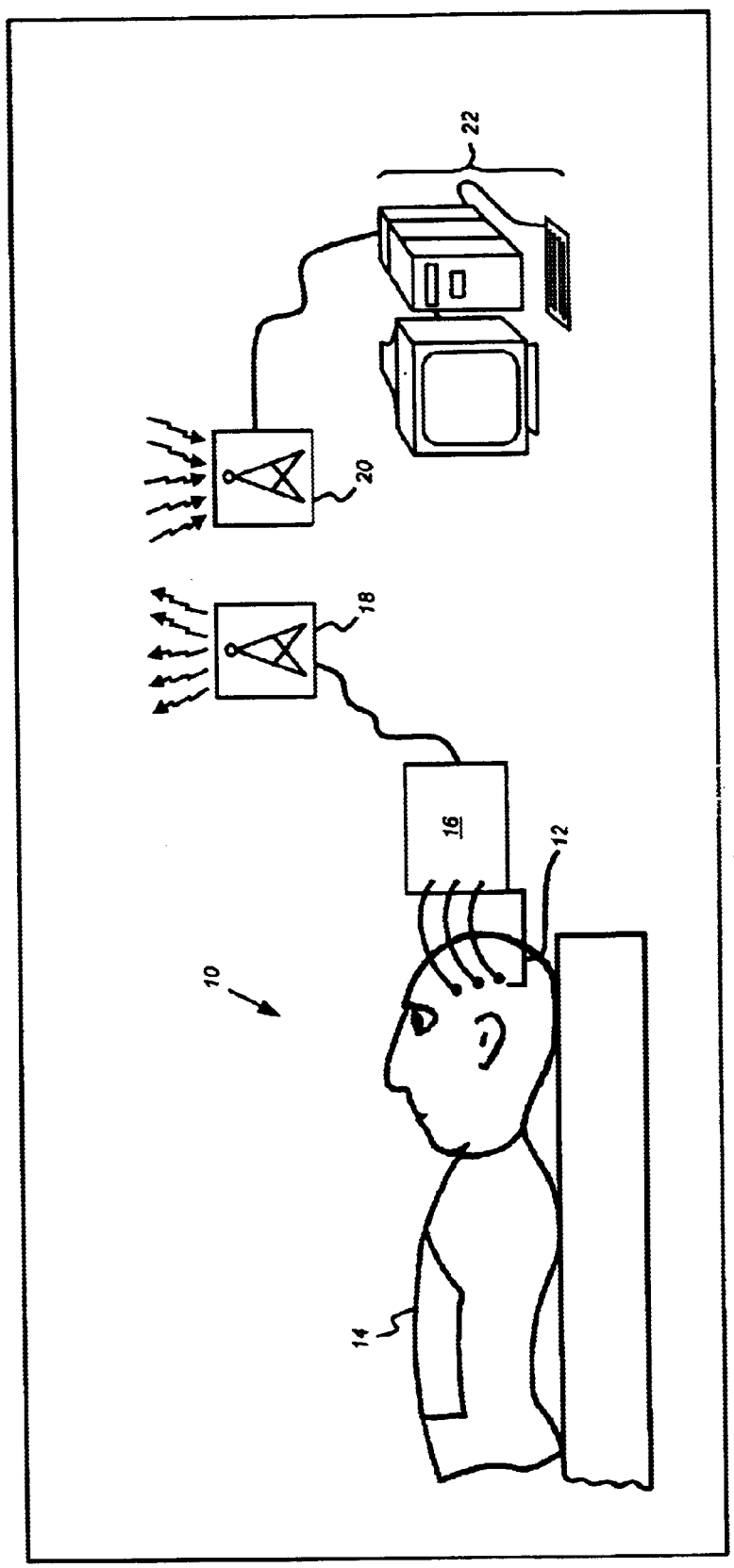
FIG. 1 is an illustration of the use of a data acquisition system according to the present invention to acquire neurological signal data from a hospital patient.

Turning first to FIG. 1, a neurological data acquisition system 10 according to the present invention, has probes 12 attached to the head of a patient 14 and inserted at selected locations of the brain. The probes are connected to an electrical-neurological detection device hereafter referred to as the "cube" 16, illustrated in more detail in FIGS. 5–13. An analog transmitter 18 is used to broadcast information to a receiver 20. The receiver is connected to a data processing station 22.

The probes 12 are used to monitor synaptic response ("spikes") using electrodes. Such electrodes can be glass tubes filled with electrolyte, gold wires, sharpened tungsten wires, or etched silicon. Alternatively, various probes may be used to monitor electroencephalographic ("EEG") signals, electromyographic ("EMG") signals, or electrocardiographic ("EKG") signals.

The cube 16 is used to convert electrical-neurological signals to analog signal representations, amplify the analog signals, combine the amplified analog signals into a single combined signal, and send the combined signal to an analog transmitter 18 where it is broadcast as a modulated radio frequency signal. The receiver 20 is used to receive the broadcast radio frequency signal, demodulate the radio frequency signal and extract the single combined signal. The data processing station 22 is used to convert the single combined signal to a combined digital signal, de-multiplex the combined digital signal into discrete digital representations of the original electrical-neurological signals, and display or store the discrete digital representations.

The use of an analog transmitter 18 physically separates the probes 12 and data processing station 22, allowing the data processing station to be placed out of the way or in another room. Additionally, the use of the transmitter 18 results in the absence of wires between the cube 16 and the data processing station 22 which could hinder medical personnel from accessing the patient 14. The patient 14 is free to sit up, stand, or walk around with cube 16 attached to his or her head. The patient is not limited by the length of a wire to the data processing station 22; rather, the patient is limited only by the range of the transmitter 18 and receiver 20. The cube 16 is mobile and portable, allowing it to be used at a patient's home, the site of an accident, or in a battle-field environment. It is worth noting that the use of an analog transmitter 18 reduces size, weight, and power requirements of the cube 16 compared to the utilization of a digital transmitter with an associated analog-to-digital converter ("ADC").

Figure 2:
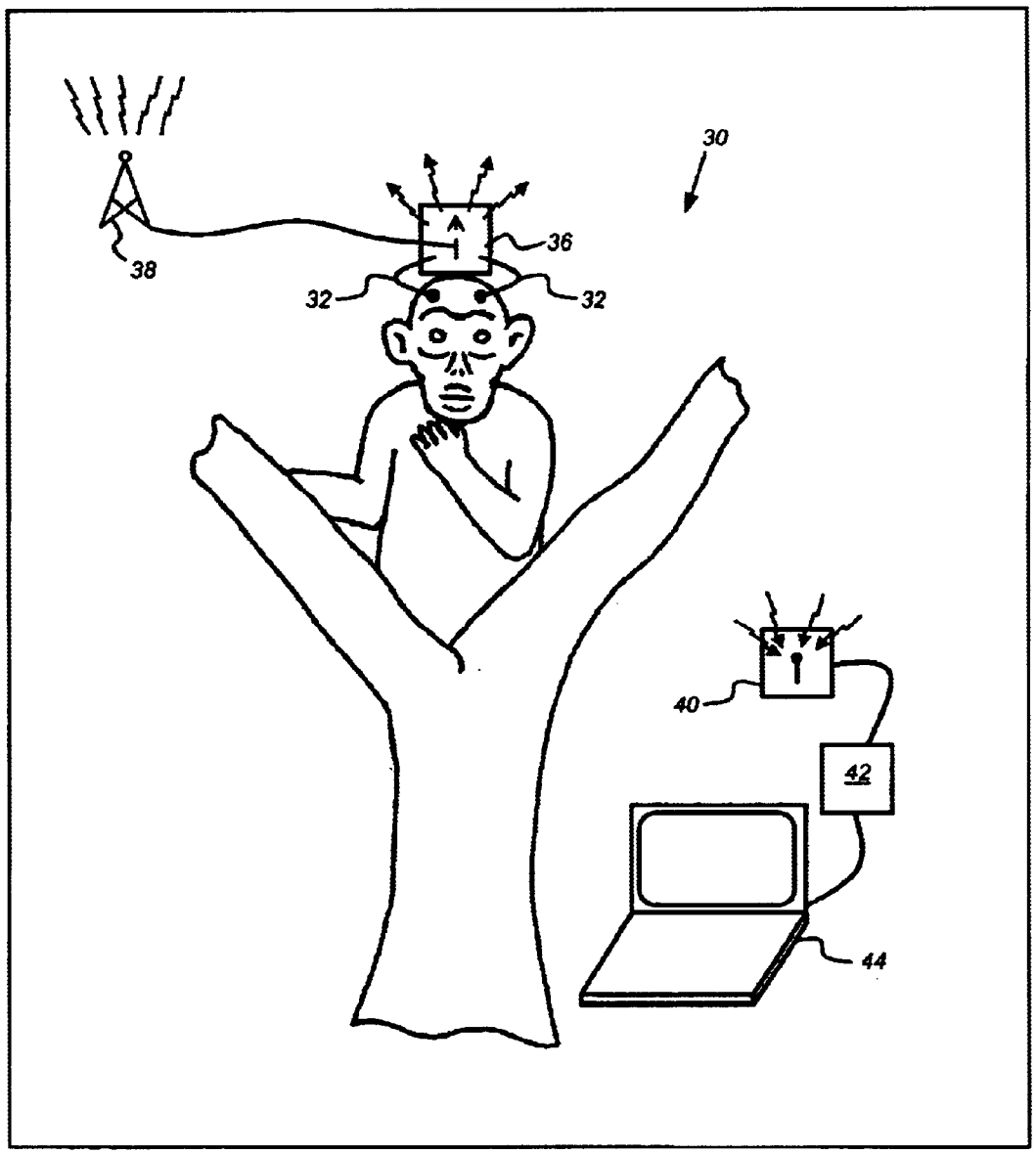
FIG. 2 is an illustration of the use of a data acquisition system according to the present invention to acquire neurological signal data from a mobile primate.

A second embodiment of the invention 30, illustrated in FIG. 2, has probes 32 attached to the head of a monkey 34. The probes are connected to a cube 36. An analog transmitter 38 is used to broadcast information to a receiver 40. The receiver is connected to an ADC 42 which is, in turn, connected to a portable computer 44.

The probes 32 are used in the same manner as probes 12 of FIG. 1, i.e., they can be used to monitor "spikes", EEG signals, EMG signals, or EKG signals. The cube 36 serves same function as cube 16 of FIG. 1. It converts electrical-neurological signals to analog signals, amplifies the analog signals, combines the amplified analog signals into a single combined signal, and broadcasts the combined signal as a modulated radio frequency signal. The receiver 40 is used in same manner as receiver 20 in FIG. 1. It receives the broadcast radio frequency signal, demodulates the radio frequency signal and extracts the combined analog signal. The ADC 42 is used to convert the combined analog signal to a combined digital signal. The portable computer 44 is used to de-multiplex the combined digital signal into discrete digital representations of the original electrical-neurological signals and displays or stores the discrete digital representations. This embodiment of the data acquisition system 30 allows the cube 36 to be mobile (not constrained by wires connected to the portable computer 44) and the portable computer 44 to be easily carried to remote locations, whereas typical neurological data acquisition systems are too complex and bulky to be set up and operated effectively in a non-laboratory environment. Since the probes 32 and the data processing station 44 are separated, a test animal is free to move about in its natural environment while information is being gathered by the data acquisition system 30. Since it has long been thought that research in a laboratory setting makes the results of many scientific experiments suspect, experiments conducted in an animal's natural surroundings would provide the opportunity for increased significance and insight.

Figure 3:
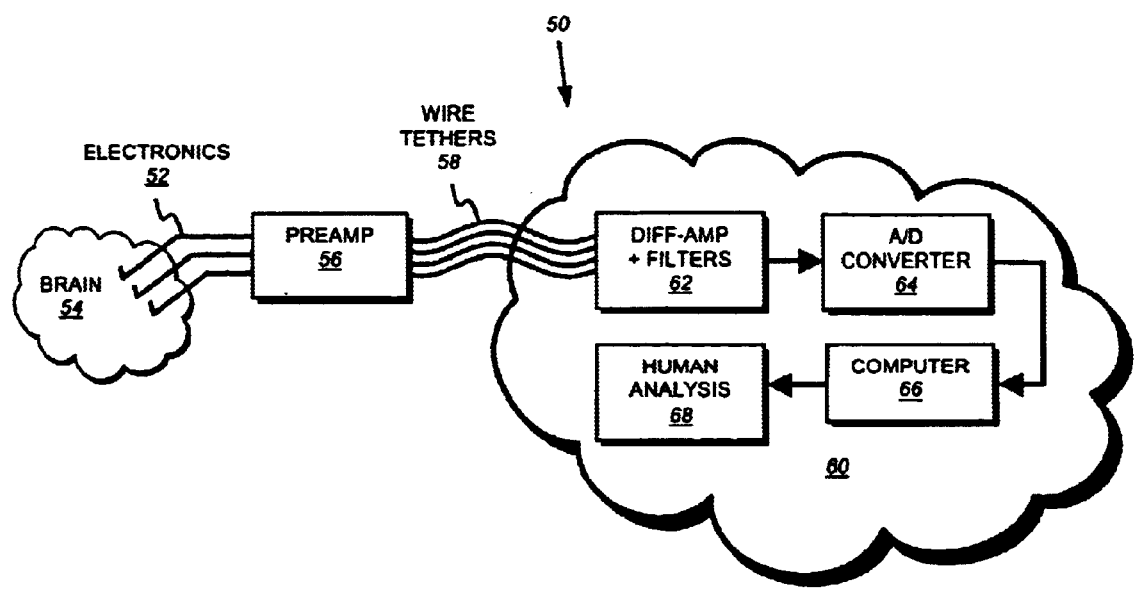
FIG. 3 is a functional block diagram of a typical neurological data acquisition system currently known in the art.

A conventional neurological data acquisition system 50 is illustrated by the functional block diagram of FIG. 3, wherein electrodes 52 are inserted into an animal's brain 54 and connected to a pre-amplifier 56. The pre-amplifier 56 is connected by wire tethers 58 to a data processing station 60. The first stage of the data processing station is an amplifier circuit 62. The output from the amplifier circuit is directed to the ADC 64. The digital output of the ADC is utilized by a computer 66 to provide a display 68 of information for human analysis.

The electrodes 52 and pre-amplifier 56 are located at the head of the animal. The physical distance between the animal and data processing station 60 is limited to the length of the wire tethers 58, restricting the mobility and range of motion of the animal. Additionally, this conventional neurological data acquisition system 50 is not portable.

Figure 4:
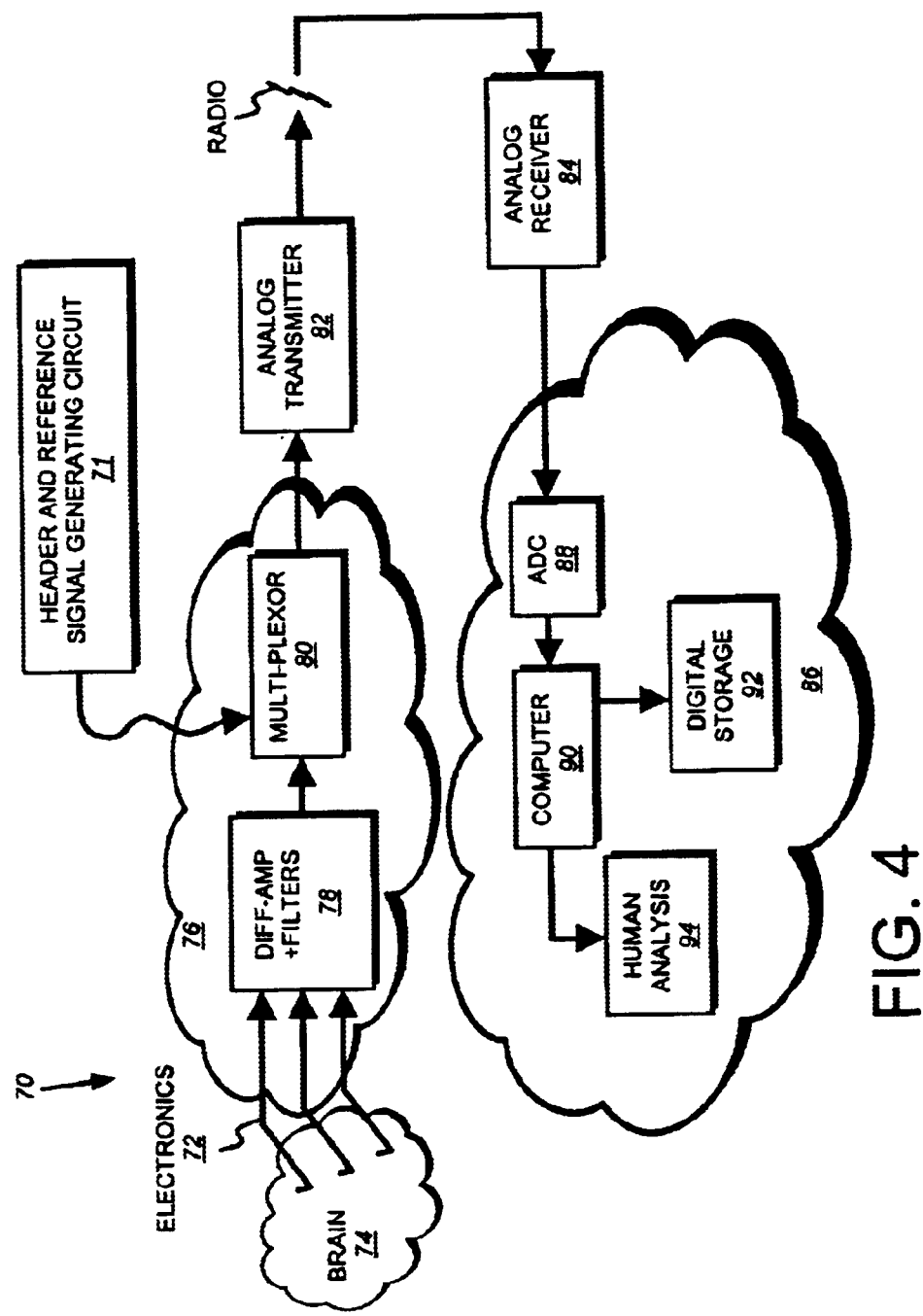
FIG. 4 is a functional block diagram of a data acquisition system according to the present invention.

The block diagram of FIG. 4 illustrates the functionality of a neurological data acquisition system 70 according to the present invention. The electrodes 72 are inserted into the brain of an animal 74 and connected to a cube 76, producing numerous analog signals representative of electrical-neurological activity in the brain of the animal 74. The first stage of the cube is an amplifier circuit 78. The second stage of the cube is a multiplexor 80 used to combine the numerous analog signals as well as packet headers and reference signals from a header and reference signal generating circuit 71. Output from the cube is sent to an analog transmitter 82 for modulating and broadcasting the combined signal produced by the multiplexor 80. An analog receiver 84 demodulates the modulated broadcast signal and passes the recovered combined analog signal to the data processing station 86. An ADC 88 converts the combined analog signal to a combined digital signal and passes it to the computer 90 where it is de-multiplexed using software algorithms to produce discrete digital representations of the electrical-neurological signals monitored by the electrodes 72. These digital signals are either placed in digital storage 92 or sent to a display 94 for human analysis. Preferably, the amplifier boards 114 are perpendicular to the transmitter board 116, and parallel to one another, as shown in FIG. 5(a).

Figure 5B:
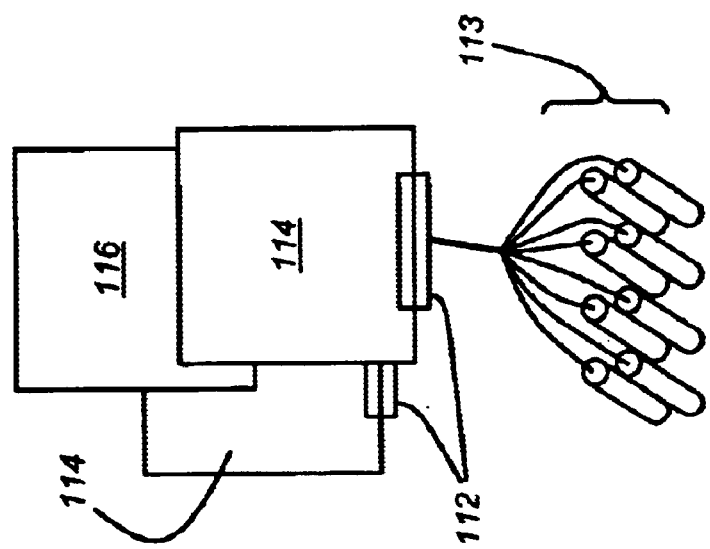
FIG. 5(b) is a perspective view illustrating a second embodiment of the physical structure of a mobile portion of the data acquisition system according to the present invention.
Figure 5A:
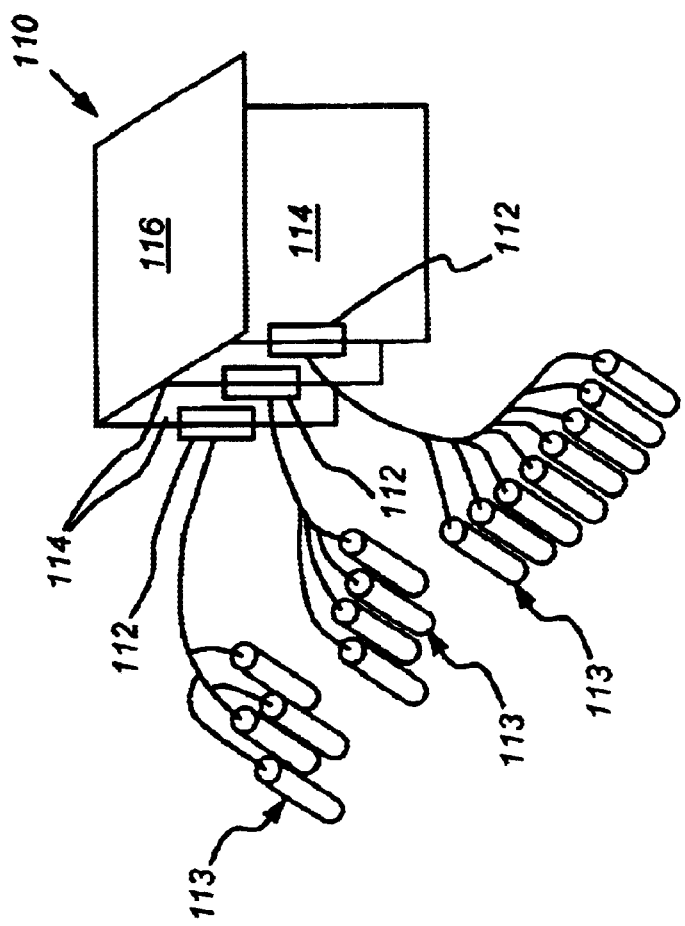
FIG. 5(a) is a perspective view illustrating a first embodiment of the physical structure of a mobile portion of the data acquisition system according to the present invention.

The structural components of a cube 110 are illustrated in FIG. 5(a). Probe connectors 112 are attached to amplifier boards 114 which are, in turn, attached to a transmitter board 116. Numerous probes 113 are attached to the amplifier boards 114 using the probe connectors 112. In the preferred embodiment of the invention, eight probes 113 are attached to each amplifier board 114. In a preferred embodiment of the invention, a transmitter board 116 is connected to eight amplifier boards 114. In FIG. 5(b), a second embodiment of the invention, a transmitter board 116 is sandwiched between two amplifier boards 114. However, the invention is not limited to only two amplifiers boards 114 and may be implemented with any number of amplifier boards 114.

The probes 113 in the preferred embodiment are high resistance, typically ½–2 mega-ohm, essentially resistive electrodes used to detect electromagnetic field signals emanating from the brain. In this case, the field signals of interest are synaptic response spikes, which are typically in the 100 micro-volt range. A typical application of this invention would require a large number of electrodes, from 16 to several hundred. However, this inventive concept applies to any plurality of electrodes. The shape and duration of each synaptic response spike requires that the field signals be monitored using analog technology. Different probes can be utilized to detect EEG, EMG, and EKG signals.

Figure 6:
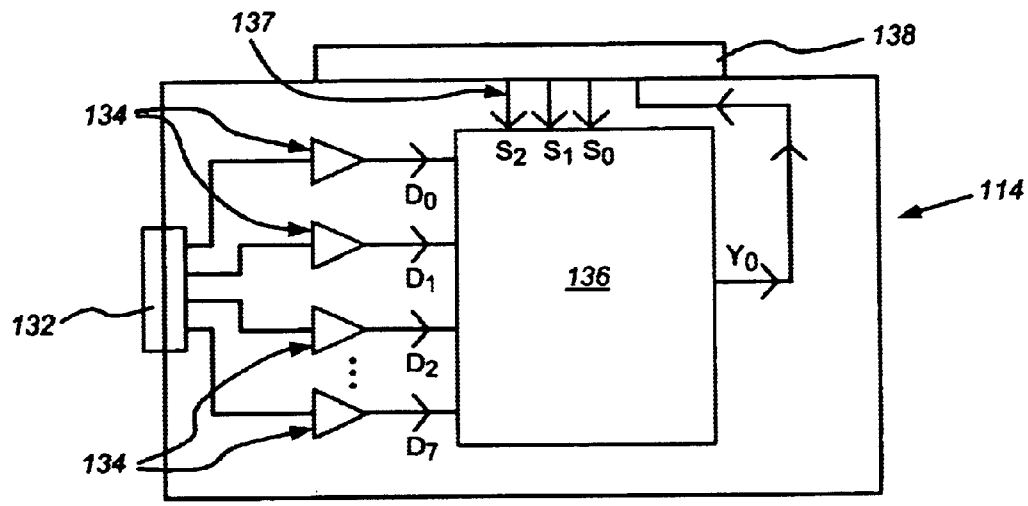
FIG. 6 is a block diagram of an amplifier board in the mobile portion according to the present invention.

The synaptic response spikes of interest are in the range of 100 micro-volts. As a single channel analog transmitter is to be used in the preferred embodiment, the numerous signals produced by the numerous probes must be multiplexed together. Because multiplexing signals of such small magnitude is at best impractical, it is necessary to first amplify these signals. FIG. 6 is a block diagram illustrating the amplifier board 114 of FIG. 5. A wire from each probe and a wire from a reference probe are inserted into the probe connector 132. Each pair of wires is provided as an input to a differential amplifier 134. The differential amplifiers 134 increase the magnitude of the signal provided by the probes. The output of the differential amplifiers 134 is sent to a multiplexor 136. The preferred embodiment uses eight differential amplifiers 134 for each amplifier board 114.

Figure 7:
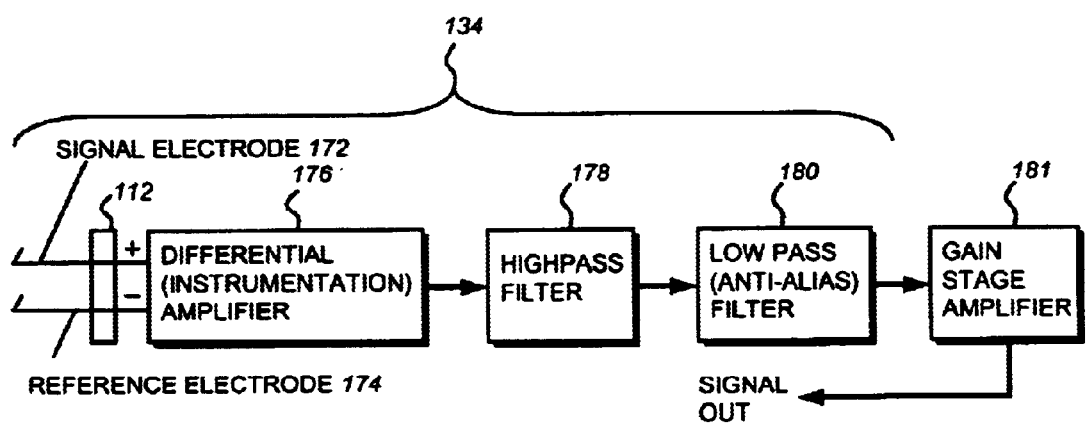
FIG. 7 is a block diagram of a differential amplifier and filters included in the amplifier board of FIG. 6.

Turning to FIG. 7, the differential amplifier and filter 134 referred to in FIG. 6 is illustrated using a block diagram. A signal electrode 172 and a reference electrode 174 are connected to a probe connector 112, shown in FIG. 5. The signal electrode 172 and the reference electrode 174 are used as inputs to a differential amplifier 176. A high-pass filter 178 is used to remove low frequency EEG signals which can be up to a hundred times greater in magnitude than the synaptic response spikes of interest. A low-pass filter 180 is used to provide signal anti-aliasing prior to sending it to a multiplexor. Anti-aliasing is necessary due to the mathematical nature of multiplexors. A gain stage amplifier 181 is used to further increase the signal strength. The combined gain of the differential amplifier and filter circuit is approximately three thousand in the preferred embodiment. The result is an analog signal representation of the synaptic response field signals with a peak-to-peak range of typically about six tenths of a volt, which is sufficient for detection and manipulation.

In the preferred embodiment, eight probes 113 are attached to a probe connector 112 of each amplifier board 114. Each of these probes is amplified using a differential amplifier and filter circuit 134 shown in FIG. 7. As mentioned previously, use of a single channel transmitter requires that the signal information from several probes be combined together. To accomplish this, multiplexors are used. A first level multiplexor 136, shown in FIG. 6, is located on each of the amplifier boards 114. The inputs to the first level multiplexor 136 come from each of the differential amplifier and filter circuits 134. The output of the first level multiplexor 136 is one of any of the numerous inputs, depending on the values on the select lines 137 controlling the multiplexor 136. The output of the first level multiplexor 136 is routed to the transmitter board connector 138 which is inserted into the transmitter board 116 of FIG. 5. Select lines 137 controlling the multiplexor 136 are routed from the transmitter board connector 138 to the multiplexor 136.

Figure 8:
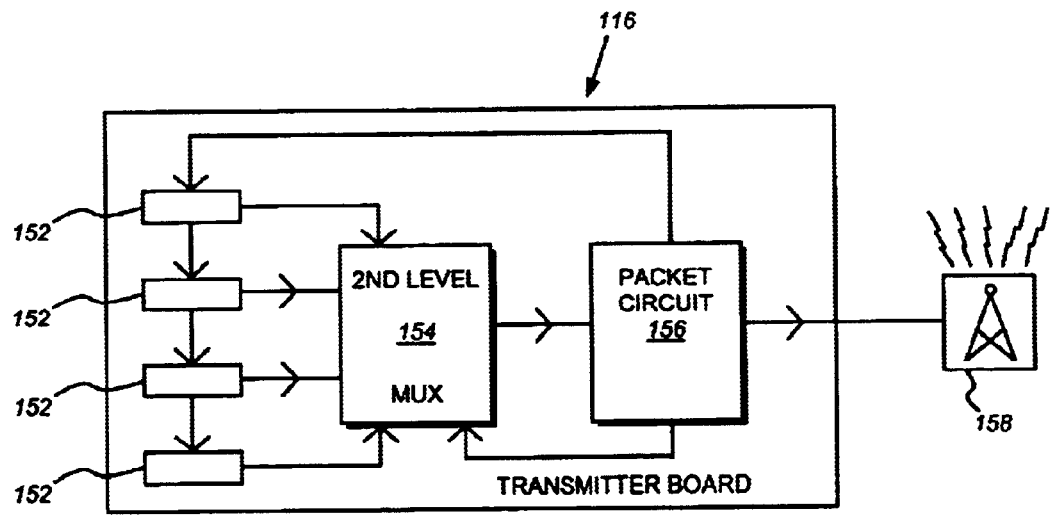
FIG. 8 is a block diagram of a transmitter board according to the present invention.

Turning to FIG. 8, which is a block diagram of the transmitter board 116 of FIG. 5, amplifier board connectors 152 are used to join the transmitter board 116 to the amplifier boards 114 of FIG. 6. Multiplexed signals from each amplifier board 114 arrive through the amplifier board connectors 152 and are passed to a second level multiplexor 154. The output of the second level multiplexor 154 is sent to the packet generator circuit 156 where it is prepared for transmission. The signal is then sent to an analog transmitter 158 which modulates the output of the packet generator circuit 156 and broadcasts it as a radio frequency signal.

The preferred embodiment of the invention will have up to eight amplifier boards 114 attached to the transmitter board 116. A multiplexed signal is provided from each of the amplifier boards 114, requiring a second level multiplexor 154 to combine them. Inputs to the second level multiplexor 154 arrive from each of the populated amplifier board connectors 152. Any one of these inputs may be selected as the output of the second level multiplexor 154, depending on the state of select lines controlled by the packet generation circuit 156.

A receiver must be able to identify the start and finish of messages sent by the analog transmitter. This requires that an analog transmitter and an analog receiver have a means for synchronizing information transfer. There is an additional need to offset any DC bias between the transmitter 18 of FIG. 1 and the receiver 20 of FIG. 1 due to normal effects of radio signal transmission, such as signal strength changes and multi-path reflections of the RF energy/signal. The packet generation circuit 156 is used to group information from numerous probes into a communication packet to be transmitted, while providing a DC bias offset correction.

A communication packet has a formal composition including a header and several frames of data, each frame representative of an individual probe signal. The header is a unique and recognizable waveform at the start of each packet. The header waveform is used by the transmitter 18 and the receiver to "handshake", ensuring that the receiver 20 can discern the beginning of a new packet. The packet handshaking method is user definable and re-configurable. This handshaking also allows the data processing station 22 to adjust for varying signal strength from the radio as an animal or patient moves, which would otherwise skew the value of the data being transmitted. In order to avoid drift between the analog transmitter 18 and the receiver 20, an inverting unity gain amplifier is utilized to invert alternating headers and alternating data packets such that alternating groups of signals from the device will be inverted. This effectively ensures that the average value of the packet outline is zero and negates any effects of the AC-coupled transmitter.

It has been found that commercially-available low power analog video transmitters are particularly suitable for transmitting the multiplexor signal the receiver 20. For example, an off-the-shelf analog video transmitter can consume less than 100 milliwatts of power. As analog radios typically operate in the 1-volt range, a 100 micro-volt synaptic response signal must be amplified and filtered as previously described. By use of multiplexed analog transmitters, A-D conversion can now be deferred to the receiving end of the system, greatly reducing the complexity, size, weight, and power requirement of the detection and transmission hardware. Additionally, the selection of a low-power analog transmitter allows for a considerable increase in range, compared to a digital system, while reducing the size and weight of batteries used to power the device. In the preferred embodiment of the neurological data acquisition system 10, the analog transmitter 18 is used to modulate information packets and broadcast them using a single channel radio frequency carrier wave.

Figure 9:
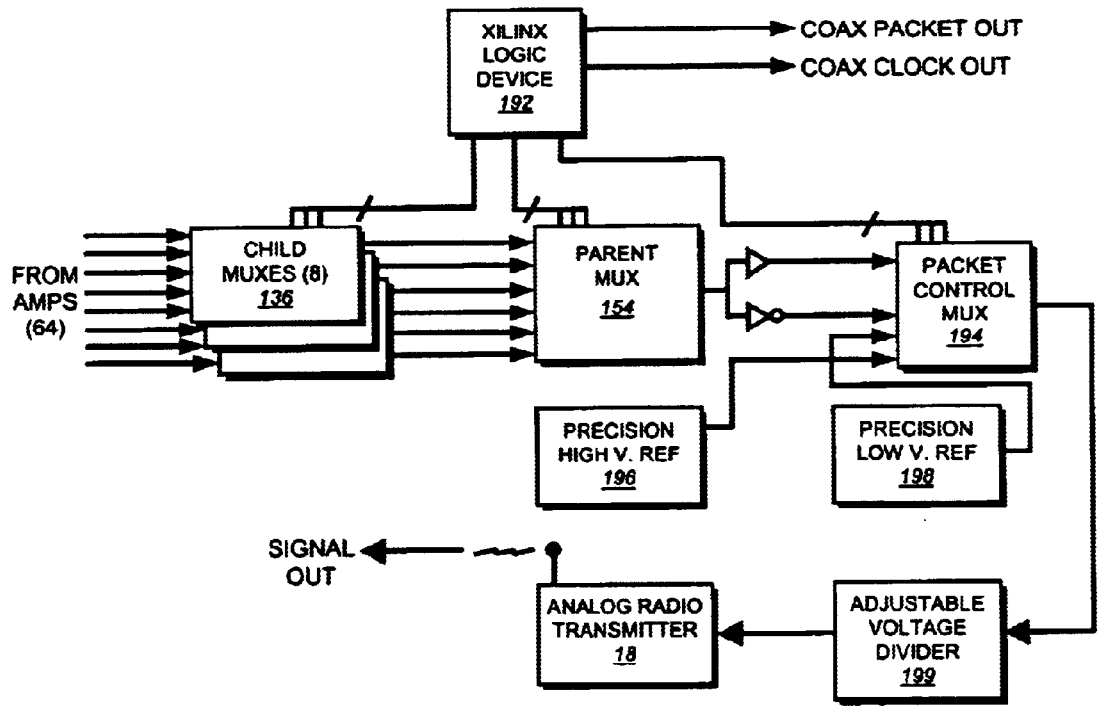
FIG. 9 is a block diagram of a multiplexor circuit encompassing a first level and a second level multiplexor, as well as packet generation hardware, according to the present invention.

Hardware required to generate communication packets is illustrated in FIG. 9. A complex programmable logic device 192 ("CPLD") provides control signals to the first level multiplexors 136, the second level multiplexor 154, and a packet control multiplexor 194. The packet control multiplexor 194 is necessary to cycle through several high-low values determined by two precision tolerance voltage references, a precision high voltage reference 196 and a precision low voltage reference 198, before polling data from each of the probes 12. An adjustable voltage divider 199 is provided in case the amplifier gain proves too high for the analog transmitter 18.

Figure 10A:
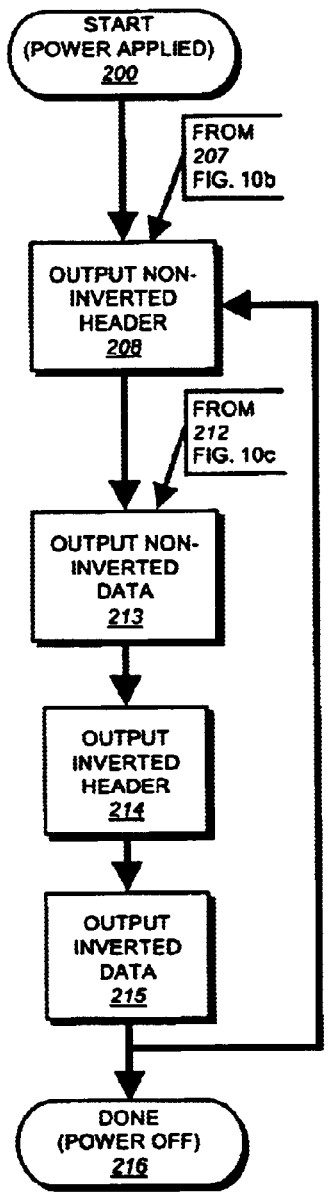
FIG. 10(a) is a first portion of a data flow diagram of a multiplexor circuit according to the present invention.
Figure 10B:
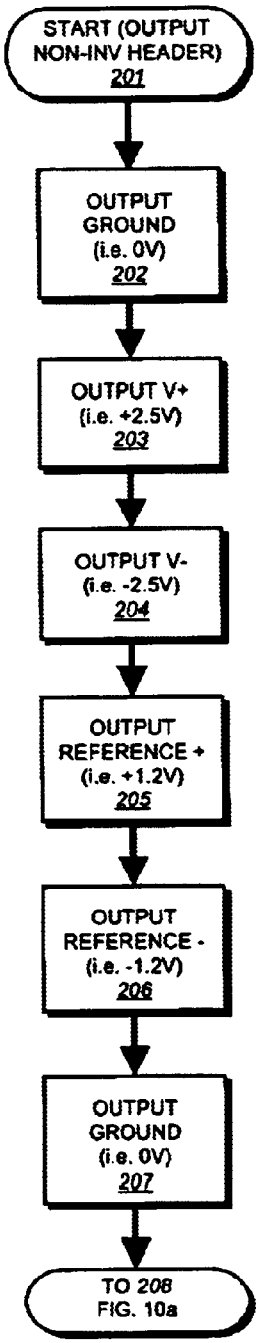
FIG. 10(b) is a second portion of a data flow diagram of a multiplexor circuit according to the present invention.
Figure 10C:
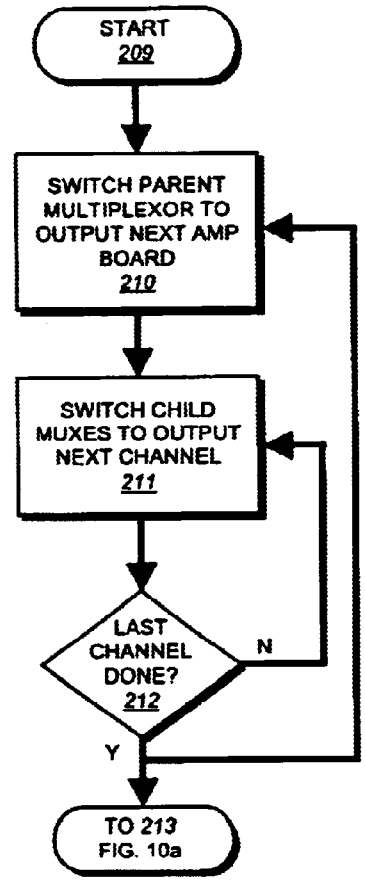
FIG. 10(c) is a third portion of a data flow diagram of a multiplexor circuit according to the present invention.

FIGS. 10(a)–10(c) are a flow diagram illustrating the packet generation sequence. Starting with FIG. 10a, when generating data packets, step 200 indicates power is applied to the packet generation circuit 156 shown in FIG. 8. Algorithms depicting header generation and data generation are shown in FIGS. 10(b) and 10(c) and described below. Once a header has been generated, using the algorithm of FIG. 10(b) for the preferred embodiment, a non-inverted header is output from the packet generation circuit 156 in step 208. Non-inverted data accumulated using the algorithm of FIG. 10(c) is output from the packet generation circuit 156 in step 213. The packet generation circuit 156 generates the next header using the algorithm of FIG. 10(b), inverts the header, and outputs the resulting inverted header in step 214. Likewise, the next accumulated data generated by the algorithm of FIG. 10(c) is inverted and output from the packet generation circuit 156 in step 215. The process of FIG. 10(a) repeats until power is removed from the packet generation circuit 156 in step 216.

FIG. 10(b) illustrates the process of forming a header according to the preferred embodiment of the invention. Beginning with step 201, a ground level signal is generated in step 202. This is followed by a generated positive voltage of typically 2½ volts in step 203 and followed by a generated negative voltage of typically 2½ volts in step 204. An output reference signal of positive 1.2 volts is generated in step 205 followed by a negative reference signal of negative 1.2 volts in step 206. Finally, a ground level signal is again generated in step 207. The header generated by this process is sent to step 208 of FIG. 10(a) for the creation of a non-inverted header and to step 214 of FIG. 10a for the creation of an inverted header.

FIG. 10(c) illustrates the process of forming an accumulation of data from the probes 113 of FIG. 5. Starting with step 209, the process selects the first amplifier board 114 in step 210. Once an amplifier board 114 has been selected, a data channel corresponding to a probe 113 is selected and sampled in step 211. Step 212 tests to verify if the selected channel is the last channel from the selected amplifier board 114. If not, the process returns to step 211 where the next channel is selected. If the channel tested in step 212 is the last channel for the amplifier board 114, then the process returns to step 210 and selects the next amplifier board 114.

Once the last channel of the last amplifier board has been sampled, the resulting accumulated data is utilized in step 213 of FIG. 10(*a*) for non-inverted data and in step 215 of FIG. 10(*a*) for inverted data generation.

Figure 11A:
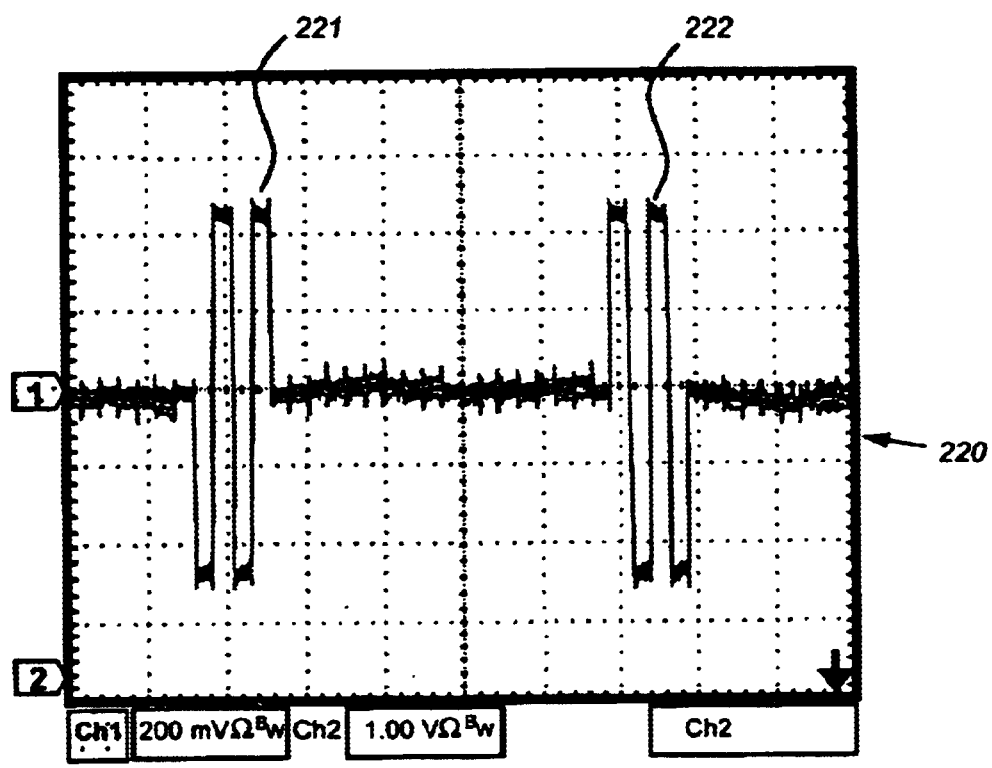
FIG. 11(a) is an oscilloscope trace illustrating headers of a packet generated by the multiplexor circuit of FIG. 9.
Figure 11B:
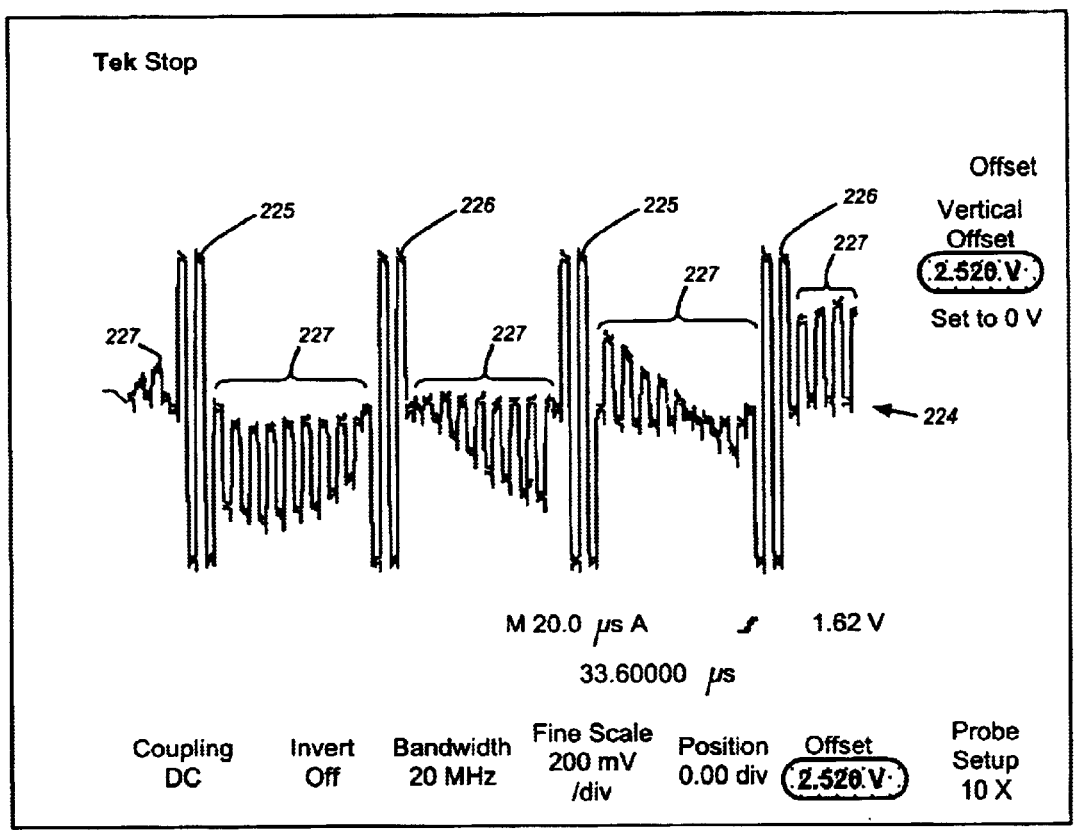
FIG. 11(b) is an oscilloscope trace illustrating headers and data of a packet generated by the multiplexor circuit of FIG. 9.

Turning to FIG. 11(*a*), an oscilloscope trace is used to illustrate the waveform 220 of an information packet generated by the packet generation circuit 156 using the process of FIGS. 10(*a*), 10(*b*), and 10(*c*). However, in this illustration, only a non-inverted header 221 and an inverted header 222 are illustrated according to the invention. The signal between the non-inverted header 221 and the inverted header 222 is simply grounded "noise" in this Figure. FIG. 11(*b*) is an oscilloscope trace 224 of an information packet generated by the packet generation circuit 156 using the process of FIGS. 10(*a*), 10(*b*), and 10(*c*). In this illustration, data 227 represented between non-inverted headers 225 and inverted headers 226.

The analog receiver 20 is used to capture the broadcast modulated carrier signal generated by the analog transmitter 18. The receiver 20 demodulates the carrier signal and extracts a combined analog signal, i.e., the information packet containing the header and frames of data containing the amplified signals representative of the electrical-neurological probes.

Figure 12:
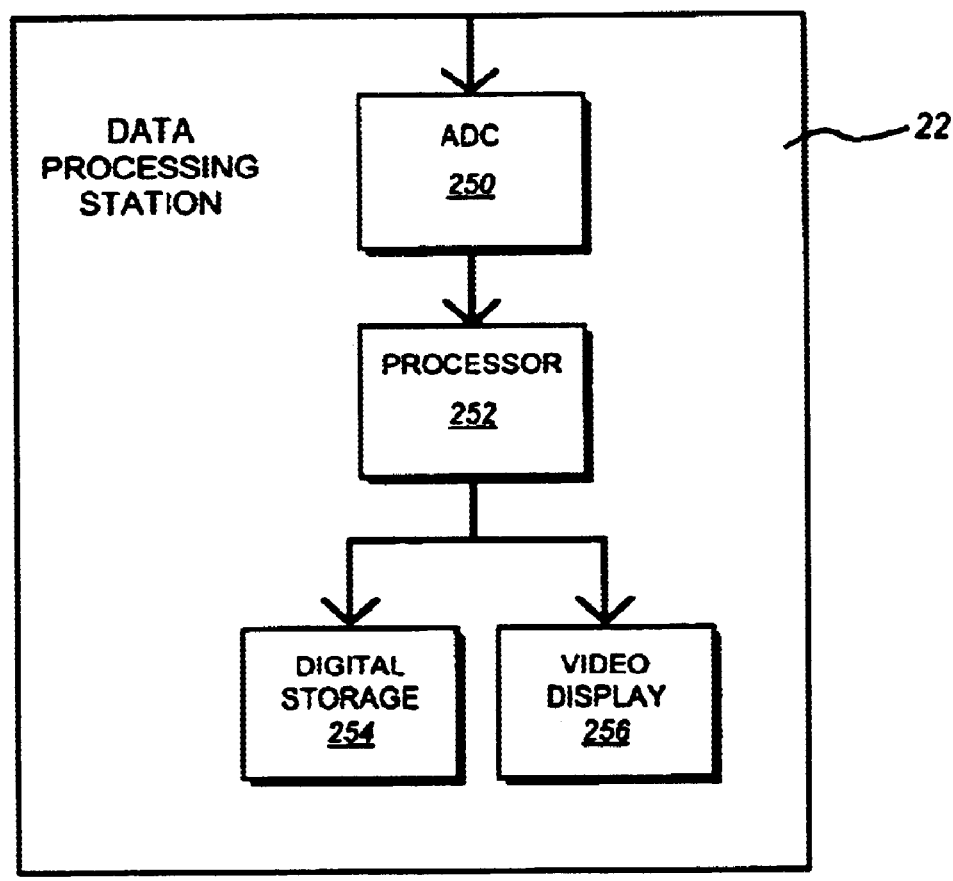
FIG. 12 is a block diagram of a data processing station according to the present invention.

The analog signal is then sent to an ADC 250 which is a component of the data processing station 22 of FIG. 12. The digital output from the ADC 250 is then sent to a computer processor 252 where software algorithms are utilized to remove the header and demultiplex the combined signal. Utilizing a software de-multiplexor rather than a hardware de-multiplexor allows the data acquisition system to vary based on the number of probes 113 being monitored. Preferably, the packet generation circuit 156, specifically the CPLD 192, is re-programmable as well. This provides built in flexibility to the entire data acquisition system without the need to change or replace any hardware (other than the type and number of probes). The computer processor 252 places the output of the software algorithm, digital signal representations of the synaptic response spikes detected by the probes 113, into either digital storage 254 (hard drive, floppy disk, CD-ROM, etc.) or sends it to a video display 256 for human analysis.

Figure 13A:
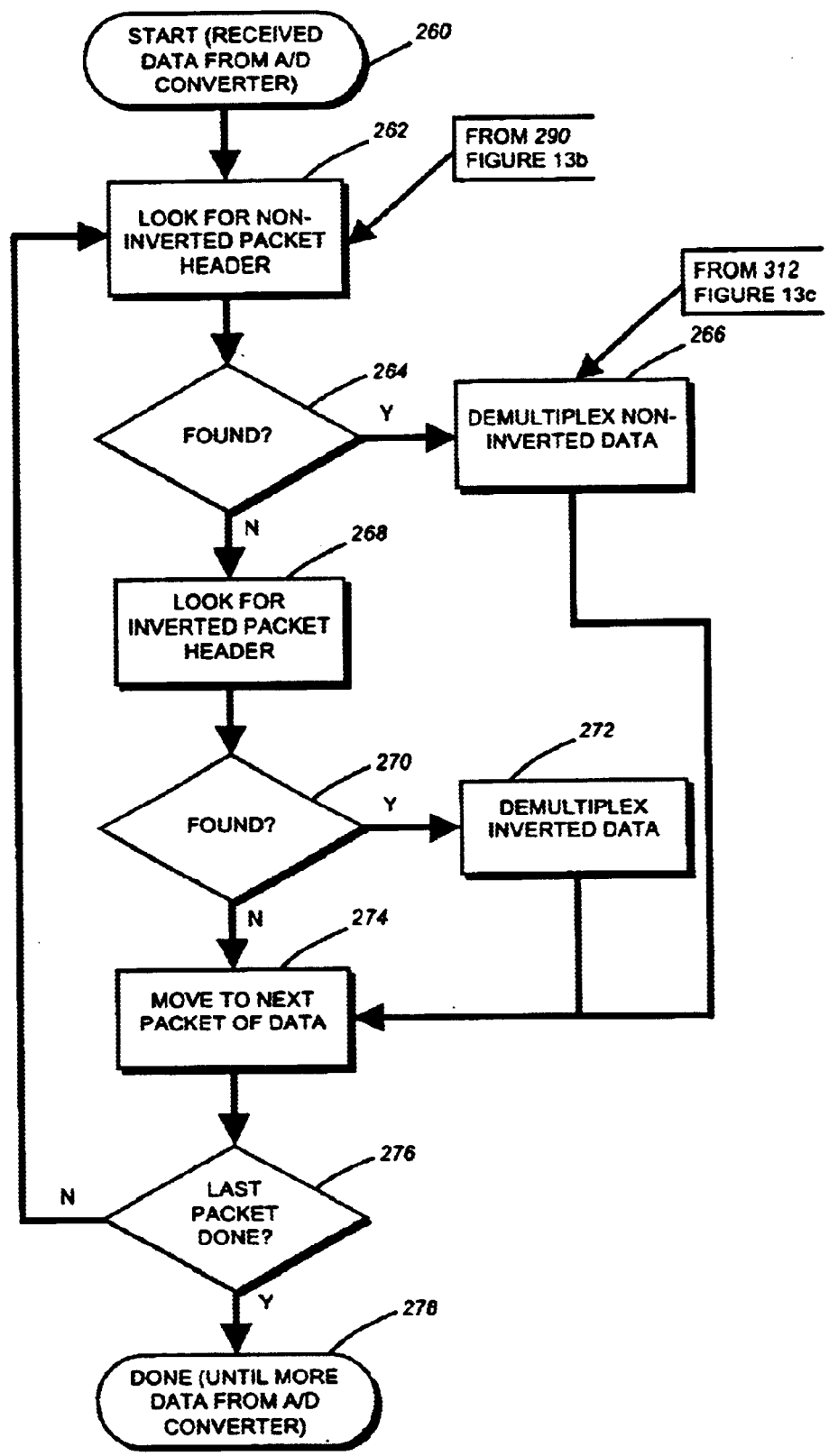
FIG. 13(a) is a first portion of a flow diagram of a de-multiplexing algorithm according to the present invention used to produce digital representations of original electrical-neurological signals.
Figure 13B:
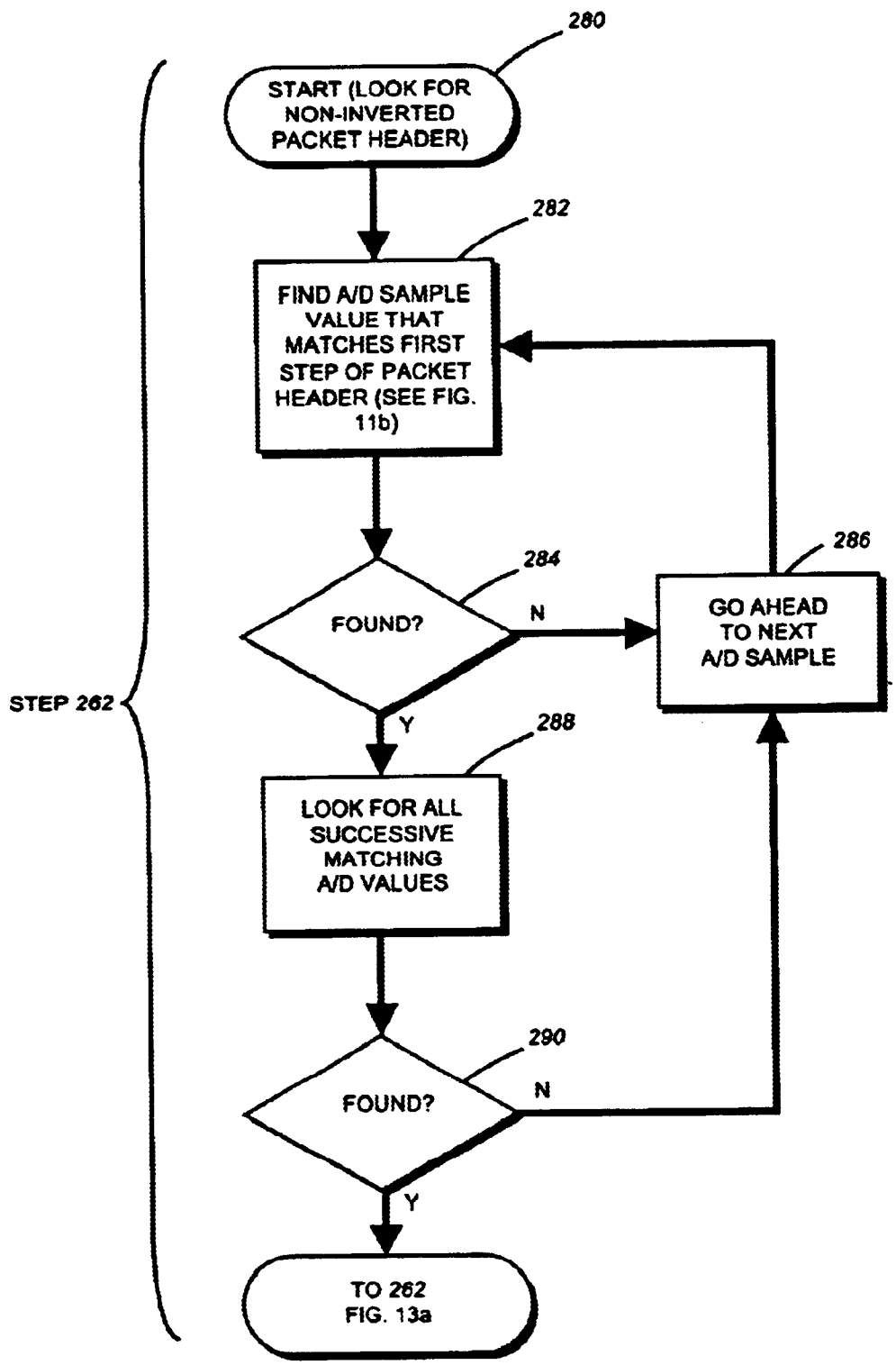
FIG. 13(b) is a second portion of a flow diagram of a de-multiplexing algorithm according to the present invention used to produce digital representations of original electrical-neurological signals.
Figure 13C:
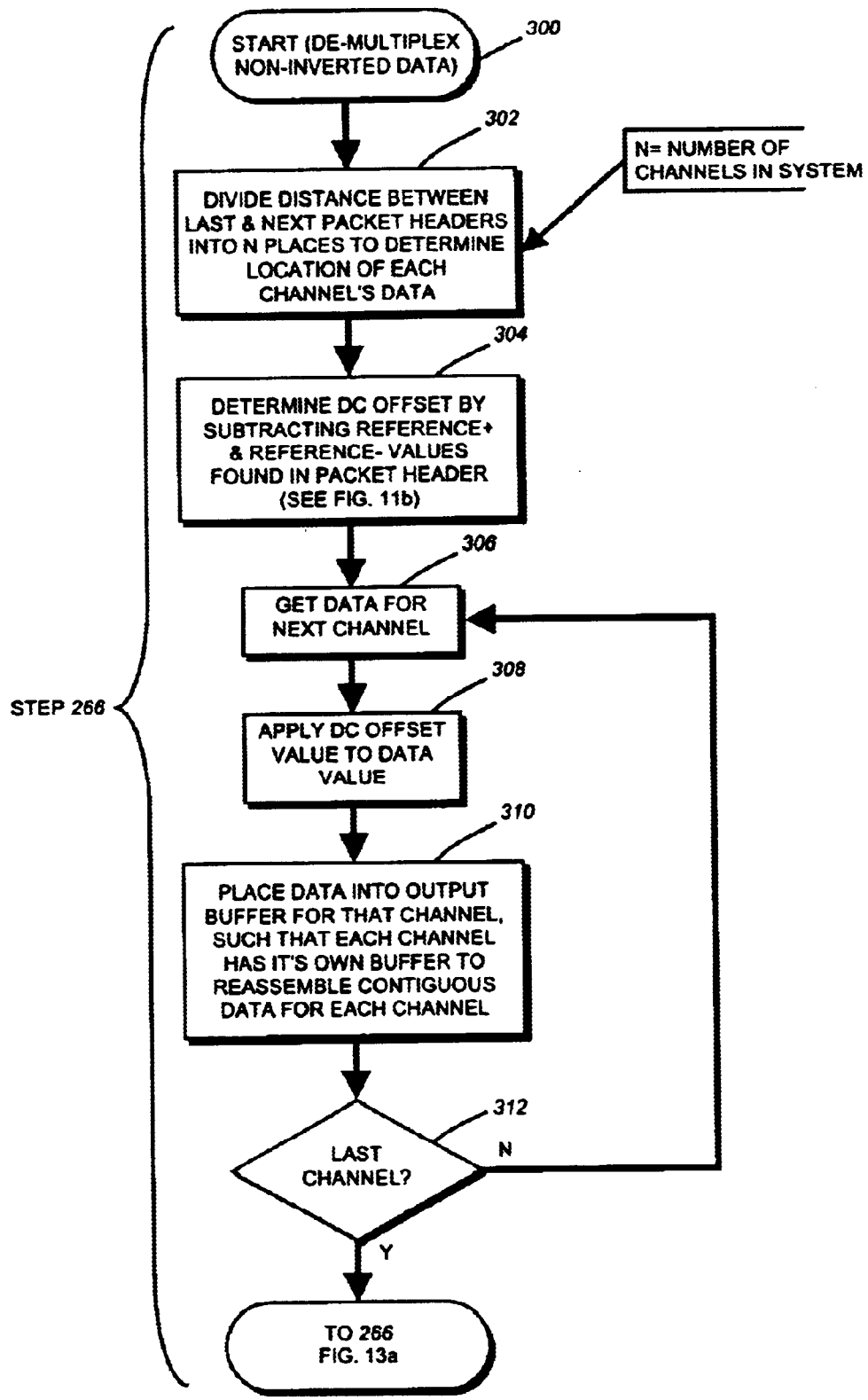
FIG. 13(c) is a third portion of a flow diagram of a de-multiplexing algorithm according to the present invention used to produce digital representations of original electrical-neurological signals.

The software de-multiplexing algorithm utilized by the computer processor 252 is illustrated in the flow chart of FIG. 13(*a*). Starting with step 250, data is received by the computer processor 252 from the ADC 250. Step 262 represents the step of looking for a non-inverted packet header. Step 262 is further illustrated by the algorithm of FIG. 13(*b*). If a non-inverted packet header is found in step 262, then the process moves to step 266 where data following the non-inverted header is de-multiplexed. Step 266 is further illustrated by the algorithm of FIG. 13*c*. If a non-inverted header is not found in step 262, then the process proceeds to step 270 where an inverted header is located using a process similar to the one in FIG. 13(*b*). Once the inverted header has been located the process proceeds to step 272 where inverted data is de-multiplexed in a process similar to the one illustrated in FIG. 13(*c*). Once a data packet has been de-multiplexed by steps 266 or 272 or if a packet header was not found by steps 262 or 268, then the process selects the next data packet and the process returns to step 262. Prior to selecting the next data packet and returning the step 262, the process tests the current data packet to verify if it is the last data packet received. If it is, the process terminates in step 278.

FIG. 13(*b*) illustrates step 262 of FIG. 13(*a*) and is similar to the algorithm used in step 268. Looking for a packet header begins in step 280. Samples of the analog signal that have been converted to digital form ("A/D sample") are examined to locate an A/D sample that matches the first voltage value of a packet header generated using the packet generation circuit 156. Once a sample matching the first voltage value of a packet header is found, the process examines subsequent A/D samples to ensure that an actual packet header has been detected as indicated in step 288. If either the first packet header value or its subsequent values are not found, the algorithm advances to the next A/D sample and the process returns to step 282. If a packet header has been successfully identified, the process returns to step 262 of FIG. 13(*a*).

FIG. 13(*c*) illustrates step 266 of FIG. 13(*a*) and is similar to the algorithm used in step 272. De-multiplexing packet data begins in step 300. The data packet between the last and the next packet headers are divided by the number of channels in the system ("N") corresponding to the number of probes 113 in step 302. DC voltage offset introduced by the packet generation circuit 156 is determined in step 304 by subtracting positive and negative reference values introduced by the algorithm of FIG. 10(*b*). The first data sample is selected in step 306 and the DC offset determined in step 304 is applied to the data sample in step 308. The resulting offset data sample is placed into one of N data buffers, each data channel representing each probe 113 having its own data buffer. Data from these data buffers is then introduced into the algorithm of FIG. 13(*a*) in step 266.

Figure 14:
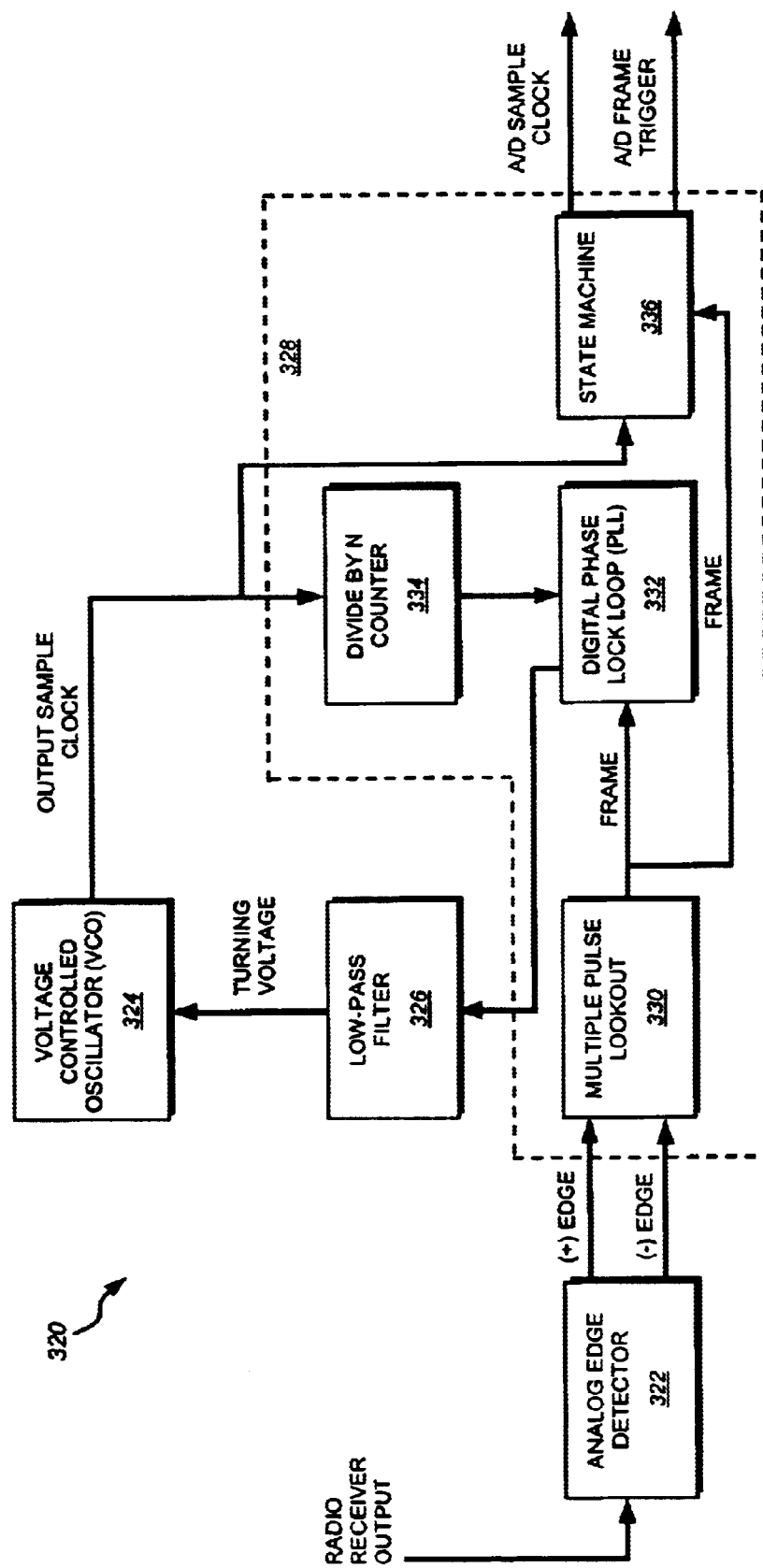
FIG. 14 is a block diagram of a frame and clock generating circuit according to the present invention.

FIG. 14 illustrates an alternative hardware device for generating a frame signal indicating the start of a new packet of information and a clock signal used to synchronize the retrieval of data from the received signal. The use of the frame and clock generating circuit 320 eliminates the need to search for headers by the computer processor 252. This eliminates the algorithmic steps of FIG. 13(*b*) to produce the results obtained in steps 262 and 268 of the algorithm of FIG. 13(*a*). Furthermore, a digital clock signal produced by the frame and clock generating circuit 320 is used by the computer processor 252 to pace the algorithm of FIG. 13(*c*) thus replacing step 302 of the algorithm. Use of the frame and clock generating circuit 320 reduces the amount of software necessary to enact the algorithms of FIGS. 13(*a*)–13(*c*) and reduce the demand on resources of the computer processor 252.

The frame and clock generating circuit 320 includes an analog edge detector 322, a voltage controlled oscillator ("VCO") 324, a low-pass filter 326, and a programmable logic device ("PLD") 328. The PLD 328 could be one of numerous kinds of programmable logic devices including FPGAs. The PLD further includes a multiple pulse lockout 330, a digital phase lock loop ("PLL") 332, a divide by "N" counter 334, and a state machine 336.

The analog edge detector 322 takes the derivative of the voltage of radio receiver output signal with respect to time and produces a large amplitude differential signal when a sudden signal change is encountered such as the beginning of a header. Output from the analog edge detector 322 is sent to the PLD 328 where it is used as the input to the multiple pulse lockout 330. Responding to the large amplitude differential signal, the multiple pulse lockout 330 produces an output signal referred to as the "frame" signal. After responding to a large amplitude differential signal from the analog edge detector 322, the multiple pulse lockout 330 ignores subsequent signals from the analog edge detector 322. The "frame" signal is used as an input by both the PLL 332 and the state machine 336. The frequency of the "frame" signal is compared to the signal arriving from the counter 334.

The PLL produces a voltage which varies as a function of this comparison. If the "frame" signal is slower than the signal from the counter 334, then the output voltage of the PLL 332 is reduced. If the "frame" signal is faster than the signal from the counter 334, then the output voltage of the PLL 332 is increased. The voltage signal output from the PLL 332 is sent to the low pass filter 326 where high frequency "ringing" is removed. The filtered, stable voltage signal is then sent to the VCO 324 to control the frequency of its output sample clock signal. This output sample clock signal is sent to the counter 334 where it is divided by the number of probes 113 in the cube 16 of FIG. 1. The number of probes in the cube 16 must be programmed into the PLD 328.

The signal output from the PLL 332, after traveling through the low pass filter 326, the VCO 324, and the counter 334, becomes a feedback signal used to compare to the frame signal produced by the multiple pulse lockout 330. The output sample clock signal produced by the VCO 324 is also used as an input to the state machine 336. Outputs from the state machine 336 include a frame trigger signal and an A-D sample clock signal.

While the preferred embodiment of this invention is the monitoring of synaptic response "spikes" in test animals and humans using electrodes, this invention may also be used to monitor brainwave (EEG) activity, heart rhythm (EKG), and electro-motor response (EMG) in animals and humans. The invention may be used in a laboratory to monitor test animals while allowing a remote placement of the data processing equipment or allowing a greater range of motion of the test animal than was previously possible. Additionally, the invention may be used to monitor animals in their natural environment.

The invention may be used in a hospital to monitor a patient while allowing the remote placement of the data processing equipment or allowing a greater range of motion of the patient than was previously possible. The patient is able to sit-up, stand, or walk around while being monitored. The invention has the added benefit of being portable enough to be used at the home or office of a patient. Alternatively, the invention may be used at remote locations such as accident sites, battlefields, or in spacecraft.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A method for acquiring neurological signal data, comprising:
   producing a plurality of analog electrical data signals corresponding to a respective plurality of neurological data signals;
   combining said plurality of electrical data signals into a single combined analog data signal;
   modulating a radio-frequency signal by said combined data signal and transmitting said modulated radio-frequency signal;
   receiving and demodulating said radio-frequency signal so as to reproduce said combined data signal;
   demultiplexing said reproduced combined data signal and reproducing said plurality of electrical data signals representative of respective neurological signals;
   formatting said combined analog data signal to produce sets of data acquired within a common time frame and adding a header at the beginning of each said set prior to modulation of said radio-frequency signal so as to add a header at the beginning of said combined data signal and so that every header following the first header is inverted from its predecessor, said header comprising signal calibration information.

2. A method for acquiring neurological signal data, comprising:
   producing a plurality of analog electrical data signals corresponding to a respective plurality of neurological data signals;
   combining said plurality of electrical data signals into a single combined analog data signal;
   modulating a radio-frequency signal by said combined data signal and transmitting said modulated radio-frequency signal;
   receiving and demodulating said radio-frequency signal so as to reproduce said combined data signal;
   demultiplexing said reproduced combined data signal and reproducing said plurality of electrical data signals representative of respective neurological signals; and
   organizing said combined data signal into sequential data packets of alternating polarity and blocking any dc component thereof prior to modulating said radio-frequency signal.

3. A neurological signal data acquisition system, comprising:
   a plurality of neurological signal acquisition circuits for producing a respective plurality of electrical data signals representative thereof;
   a multiplexor for receiving said plurality of electrical data signals and combining them into a single combined data signal;
   a radio-frequency transmitter for receiving said combined data signal and producing a radio-frequency signal modulated thereby;
   a radio-frequency receiver for receiving and demodulating said radio-frequency signal so as to reproduce said combined data signal;
   a demultiplexor for receiving said combined data signal and reproducing said plurality of electrical data signals representative of respective neurological signals; and
   a signal formatting circuit adapted to produce sets of data acquired within a common time frame and add a header at the beginning of each said set prior to modulation of said radio-frequency signal thereby, said header comprising amplitude signal calibration information.

4. The neurological signal data acquisition system of claim 3, wherein said calibration information also comprises dc offset calibration information.

5. A neurological signal data acquisition system, comprising:
   a plurality of neurological signal acquisition circuits for producing a respective plurality of electrical data signals representative thereof;
   a multiplexor for receiving said plurality of electrical data signals and combining them into a single combined data signal;
   a radio-frequency transmitter for receiving said combined data signal and producing a radio-frequency signal modulated thereby;
   a radio-frequency receiver for receiving and demodulating said radio-frequency signal so as to reproduce said combined data signal;

a demultiplexor for receiving said combined data signal and reproducing said plurality of electrical data signals representative of respective neurological signals; and a signal formatting circuit adapted to produce sets of data acquired within a common time frame and add a header at the beginning of each said set prior to modulation of said radio-frequency signal thereby, said heater comprising amplitude signal calibration information, wherein every header following the first header is inverted from its predecessor.

6. A neurological signal data acquisition system, comprising:

a plurality of neurological signal acquisition circuits for producing a respective plurality of electrical data signals representative thereof;

a multiplexor for receiving said plurality of electrical data signals and combining them into a single combined data signal;

a radio-frequency transmitter for receiving said combined data signal and producing a radio-frequency signal modulated thereby;

a radio-frequency receiver for receiving and demodulating said radio-frequency signal so as to reproduce said combined data signal; and a demultiplexor for receiving said combined data signal and reproducing said plurality of electrical data signals representative of respective neurological signals, wherein said combined data signal is organized into sequential data packets of alternating polarity and is ac coupled from said multiplexor to said radio-frequency transmitter.

7. A compact neurological signal data acquisition assembly, comprising:

a plurality of neurological signal acquisition circuits, each corresponding to a corresponding distinct neurological signal input and being disposed on a respective, substantially-planar signal channel circuit board; and a multiplexor circuit for receiving electrical signals from said plurality of neurological signal acquisition circuits and combining said electrical signals into a single combined signal;

a radio-frequency transmitter for receiving said combined data signal and producing a radio-frequency signal modulated thereby; and a common circuit board, said multiplexor circuit and said radio-frequency transmitter being disposed on said common circuit board, said common circuit board being substantially planar and said signal channel circuit boards being supported by said common circuit board in substantially parallel relation to one another perpendicular to said common circuit board.

8. A neurological signal data acquisition system, comprising:

a plurality of neurological signal acquisition circuits for producing a respective plurality of electrical data signals representative thereof, a multiplexor for receiving said plurality of electrical data signals and combining them into a single combined data signal;

a radio-frequency transmitter for receiving said combined data signal and producing a radio-frequency signal modulated thereby;

a radio-frequency receiver for receiving and demodulating said radio-frequency signal so as to reproduce said combined data signal;

a demultiplexor for receiving said combined data signal and reproducing said plurality of electrical data signals representative of respective neurological signals, wherein said demultiplexor includes an analog-to-digital converter for converting said combined data signal to digital form and a digital processor for extracting from said combined data signal in digital form to said plurality of electrical data signals.

9. The neurological signal data acquisition system of claim 8, wherein said demultiplexor includes a frame signal generation and clock signal generation circuit.

10. A method for acquiring neurological signal data, comprising:

producing a plurality of analog electrical data signals corresponding to a respective plurality of neurological data signals;

combining said plurality of electrical data signals into a single combined analog data signal;

modulating a radio-frequency signal by said combined data signal and transmitting said modulated radio-frequency signal;

receiving and demodulating said radio-frequency signal so as to reproduce said combined data signal;

demultiplexing said reproduced combined data signal and reproducing said plurality of electrical data signals representative of respective neurological signals; and wherein said demultiplexing includes converting said combined data signal to digital form and extracting said plurality of electrical data signals from said combined data signal in digital form.

11. The method of claim 10, further comprising generating frame signals and generating clock signals to synchronize the received said plurality of electrical data signals with the transmitted said plurality of electrical data signals.

12. A method for acquiring neurological signal data, comprising:

producing a plurality of analog electrical data signals corresponding to a respective plurality of neurological data signals;

combining said plurality of electrical data signals into a single combined analog data signal;

modulating a radio-frequency signal by said combined data signal and transmitting said modulated radio-frequency signal;

receiving and demodulating said radio-frequency signal so as to reproduce said combined data signal;

demultiplexing said reproduced combined data signal and reproducing said plurality of electrical data signals representative of respective neurological signals;

formatting said combined analog data signal to produce sets of data acquired within a common time frame and adding a header at the beginning of each said set prior to modulation of said radio-frequency signal so as to add a header at the beginning of said combined data signal, said header comprising signal calibration information; and including amplitude calibration information in said header.

13. A method for acquiring neurological signal data, comprising:

producing a plurality of analog electrical data signals corresponding to a respective plurality of neurological data signals;

combining said plurality of electrical data signals into a single combined analog data signal;

modulating a radio-frequency signal by said combined data signal and transmitting said modulated radio-frequency signal;

receiving and demodulating said radio-frequency signal so as to reproduce said combined data signal;

demultiplexing said reproduced combined data signal and reproducing said plurality of electrical data signals representative of respective neurological signals;

formatting said combined analog data signal to produce sets of data acquired within a common time frame and adding a header at the beginning of each said set prior to modulation of said radio-frequency signal so as to add a header at the beginning of said combined data signal, said header comprising signal calibration information; and including dc offset calibration information in said header.

* * * * *